(12) United States Patent
Jin et al.

(10) Patent No.: US 12,677,825 B2
(45) Date of Patent: Jul. 14, 2026

(54) COMPOSITION FOR PROTECTING ISLET TRANSPLANTATION

(71) Applicant: LG CHEM, LTD., Seoul (KR)

(72) Inventors: Sang-Man Jin, Seoul (KR); Jae Hyeon Kim, Seoul (KR); Gyuri Kim, Seoul (KR); Han Sin Lee, Yongin-si (KR)

(73) Assignee: LG CHEM, LTD., Seoul (KR)

( * ) Notice: Subject to any disclaimer, the term of this patent is extended or adjusted under 35 U.S.C. 154(b) by 777 days.

(21) Appl. No.: 17/916,359

(22) PCT Filed: Mar. 31, 2021

(86) PCT No.: PCT/KR2021/004022
§ 371 (c)(1),
(2) Date: Sep. 30, 2022

(87) PCT Pub. No.: WO2021/201609
PCT Pub. Date: Oct. 7, 2021

(65) Prior Publication Data
US 2023/0148589 A1 May 18, 2023

(30) Foreign Application Priority Data
Mar. 31, 2020 (KR) ........................ 10-2020-0039408

(51) Int. Cl.
*A01N 1/126* (2025.01)
*C07D 405/12* (2006.01)

(52) U.S. Cl.
CPC ........... *A01N 1/126* (2025.01); *C07D 405/12* (2013.01)

(58) Field of Classification Search
CPC .............................. A01N 1/126; C07D 405/12
See application file for complete search history.

(56) References Cited

U.S. PATENT DOCUMENTS

| | | | |
|---|---|---|---|
| 2006/0194777 A1 | 8/2006 | Gazit et al. | |
| 2010/0197673 A1 | 8/2010 | Kim et al. | |
| 2010/0291533 A1 | 11/2010 | Kim et al. | |
| 2011/0020324 A1 | 1/2011 | Nakade et al. | |
| 2016/0051558 A1 | 2/2016 | Cho et al. | |

FOREIGN PATENT DOCUMENTS

| | | | | |
|---|---|---|---|---|
| EP | 2230238 A2 | 9/2010 | | |
| JP | 2007-506732 A | 3/2007 | | |
| KR | 10-2009-0075638 A | 7/2009 | | |
| KR | 20090075638 A * | 7/2009 | .......... | C07D 403/04 |
| KR | 10-2011-0140139 A | 12/2011 | | |
| WO | 2009/025477 A1 | 2/2009 | | |
| WO | 2009-025478 A1 | 2/2009 | | |

OTHER PUBLICATIONS

Machine translation of Kim et al., KR 20090075638 A, 199 pages. (Year: 2009).*
Choi JW, et al "Acute pancreatitis associated with pegylated interferon-alpha-2a therapy in chronic hepatitis C" Clin Mol Hepatol. ( Epub) Mar. 28, 2016, 22(1), pp. 168-171; doi: 10.3350/cmh.2016.22.1.168. (Year: 2016).*
International Search Report issued for International Application No. PCT/KR2021/004022 on Jul. 5, 2021, 6 pages.
Noguchi, Hirofumi, "Regulation of c-Jun NH2-Terminal Kinase for Islet Transplantation," J. Clim, Med., 2019, vol. 8, 1763, pp. 1-15.
Jin S.-M. et al., "Anakinra Protects Against Serum Deprivation-Induced Inflammation and Functional Derangement in Islets Isolated From Nonhuman Primates," American Journal of Transplantaion, 2017, vol. 17, pp. 365-376.
Extended European Search Report issued for European Application No. 21780603.3 on Oct. 25, 2023, 10 pages.
Jin, S.A. et al., "Beneficial Effects of Necrosis Modulator, Indole Derivative NecroX-7, on Renal Ischemia-Reperfusion Injury in Rats", Transplantation Proceedings, vol. 48, No. 1, 2016, pp. 199-204.
Hyoung, Jin Kim et al., "NecroX as a Novel Class of Mitochondrial Reactive Oxygen Species and ONOO-Scavenger", Arch Pharm Res, vol. 33, No. 11, 2010, pp. 1813-1823.
Im, Keon-Il et al., "The Free Radical Scavenger NecroX-7 Attenuates Acute Graft-versus-Host Disease via Reciprocal Regulation of Th1/Regulatory T Cells and Inhibition of HMGB1 Release", The Journal of Immunology, vol. 194, No. 11, Apr. 24, 2015, pp. 5223-5232.
Kim, Gyuri et al., "Protective Effect of a Novel Clinical-grade Small Molecule Necrosis Inhibitor Against Oxidative Stress and Inflammation During Islet Transplantation" American Journal of Transplantation, vol. 21, No. 04, Sep. 25, 2020, pp. 1440-1452.
Choi et al., Acute pancreatitis associated with pegylated interferon-alpha-2a therapy in chronic hepatitis C. Clinical and Molecular Hepatology 2016; 22:168-171.

* cited by examiner

*Primary Examiner* — Aaron J Kosar
(74) *Attorney, Agent, or Firm* — ROTHWELL, FIGG, ERNST & MANBECK, P.C.

(57) ABSTRACT

The present invention pertains to a composition having a protective effect during islet transplantation, and more specifically, to a composition containing a compound of chemical formula 1 or a pharmaceutically acceptable salt thereof, and capable of providing a protective effect against oxidative stress, inflammation, etc. during islet transplantation.

5 Claims, 7 Drawing Sheets

[Figure 1]
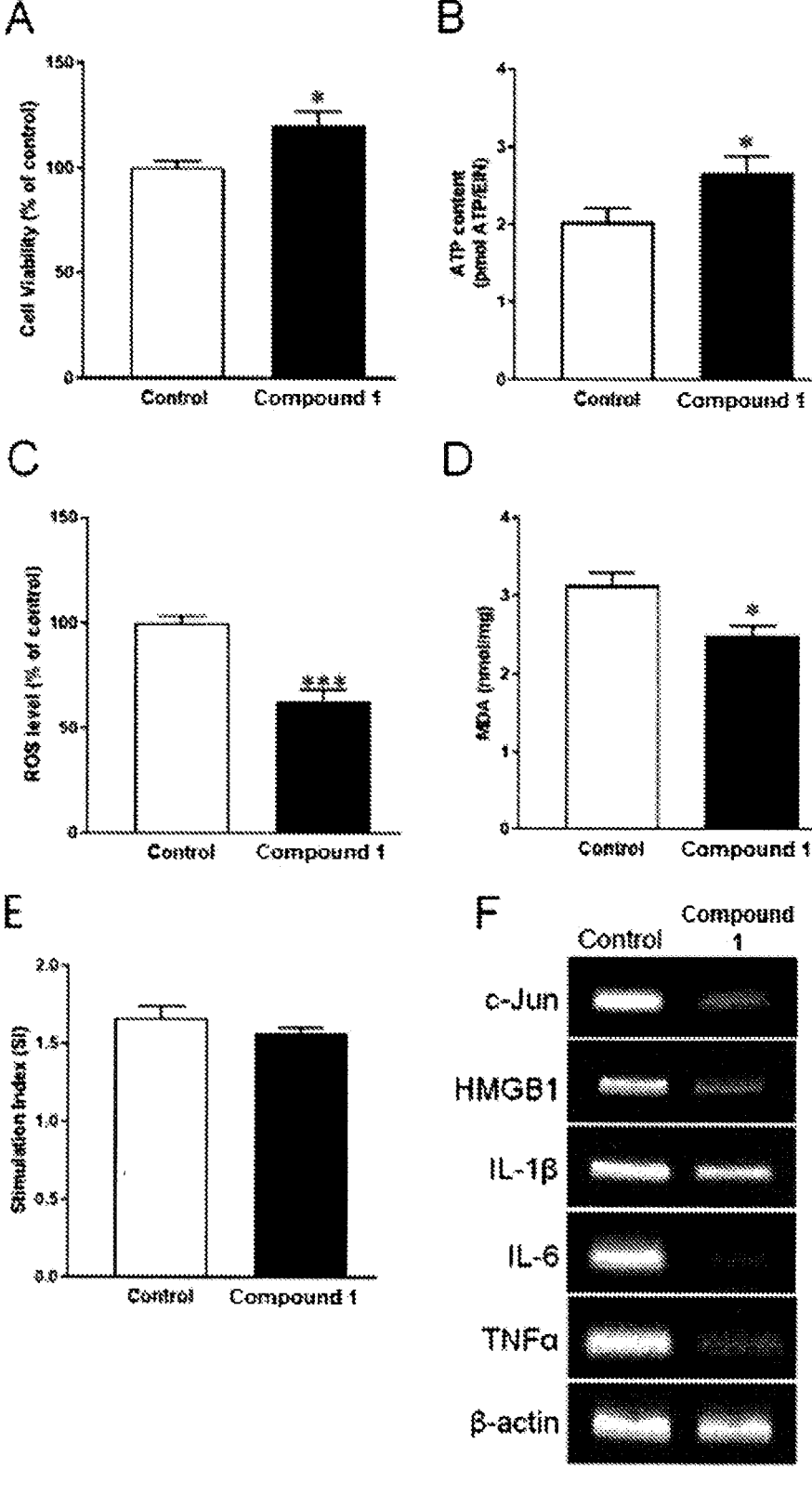

[Figure 2]
A
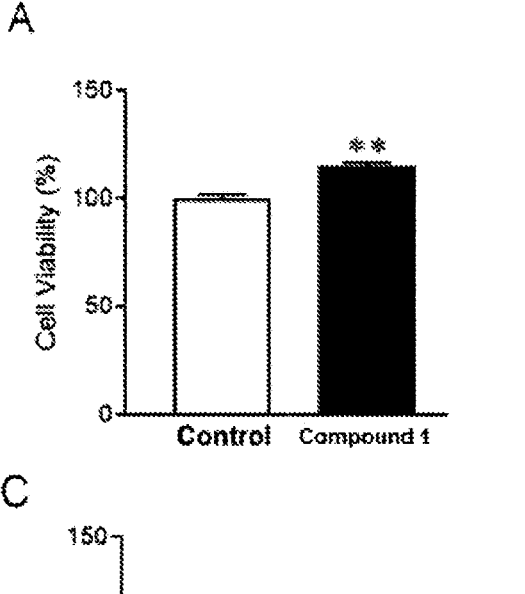
B
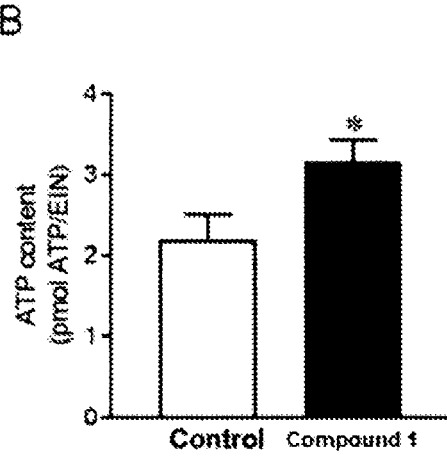
C
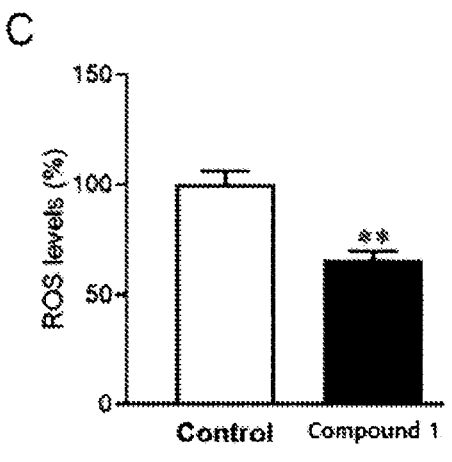
D
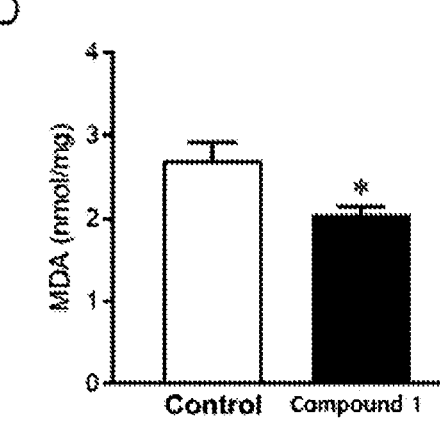
E
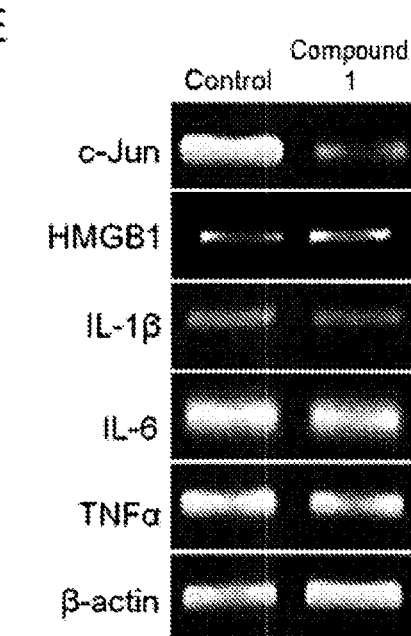

[Figure 3]

[Figure 4]
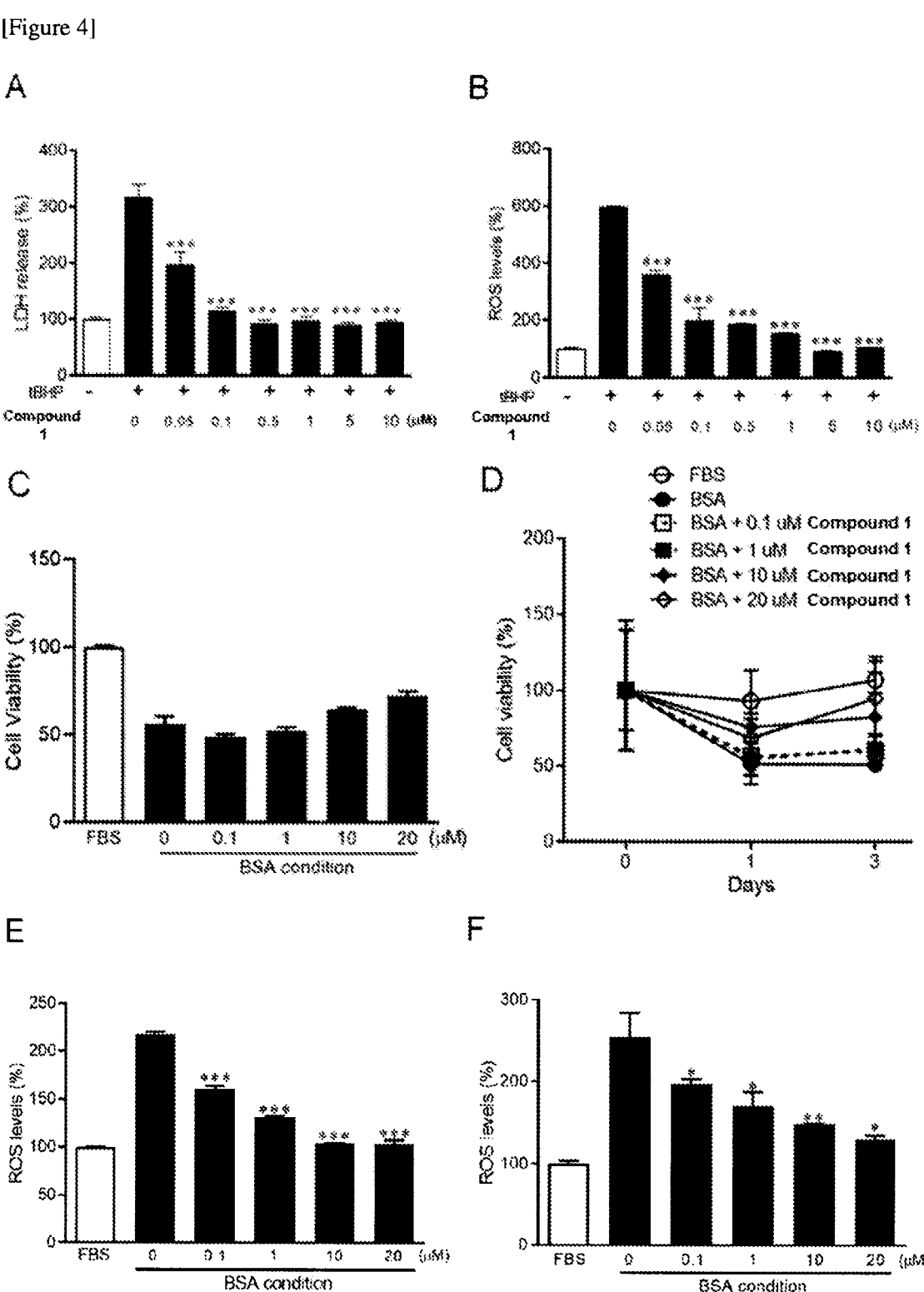

[Figure 5]
A
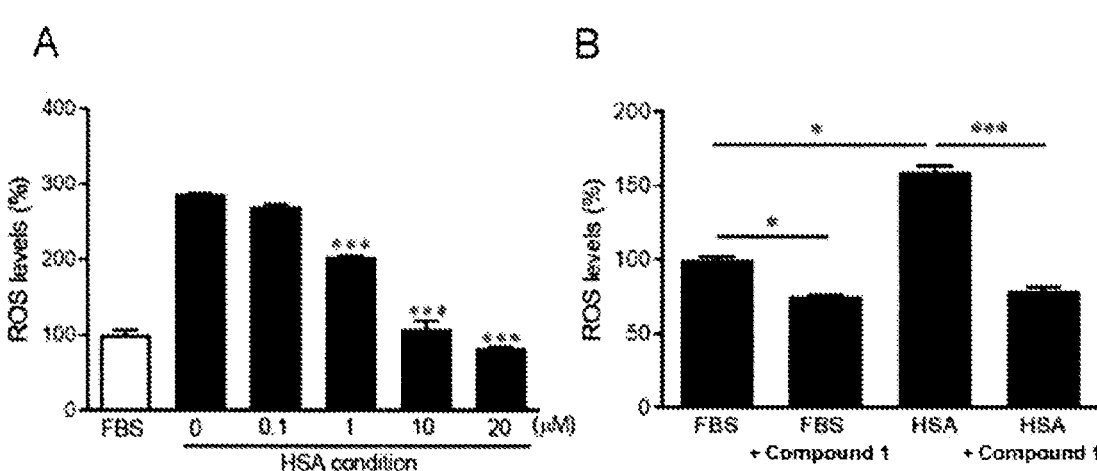
C
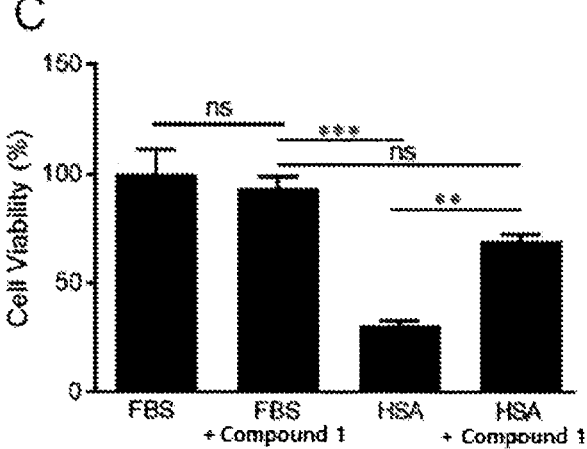

[Figure 6]
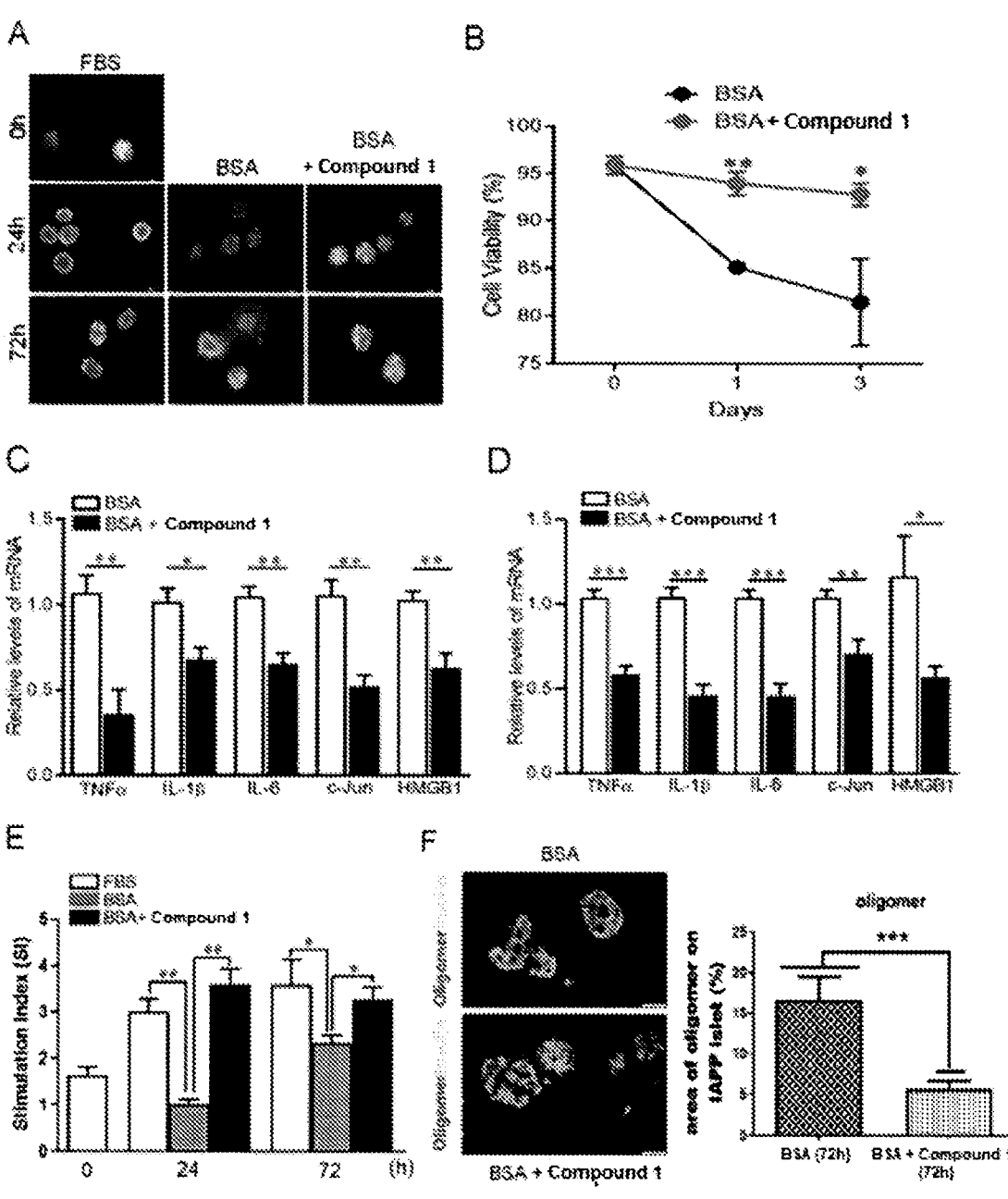

[Figure 7]
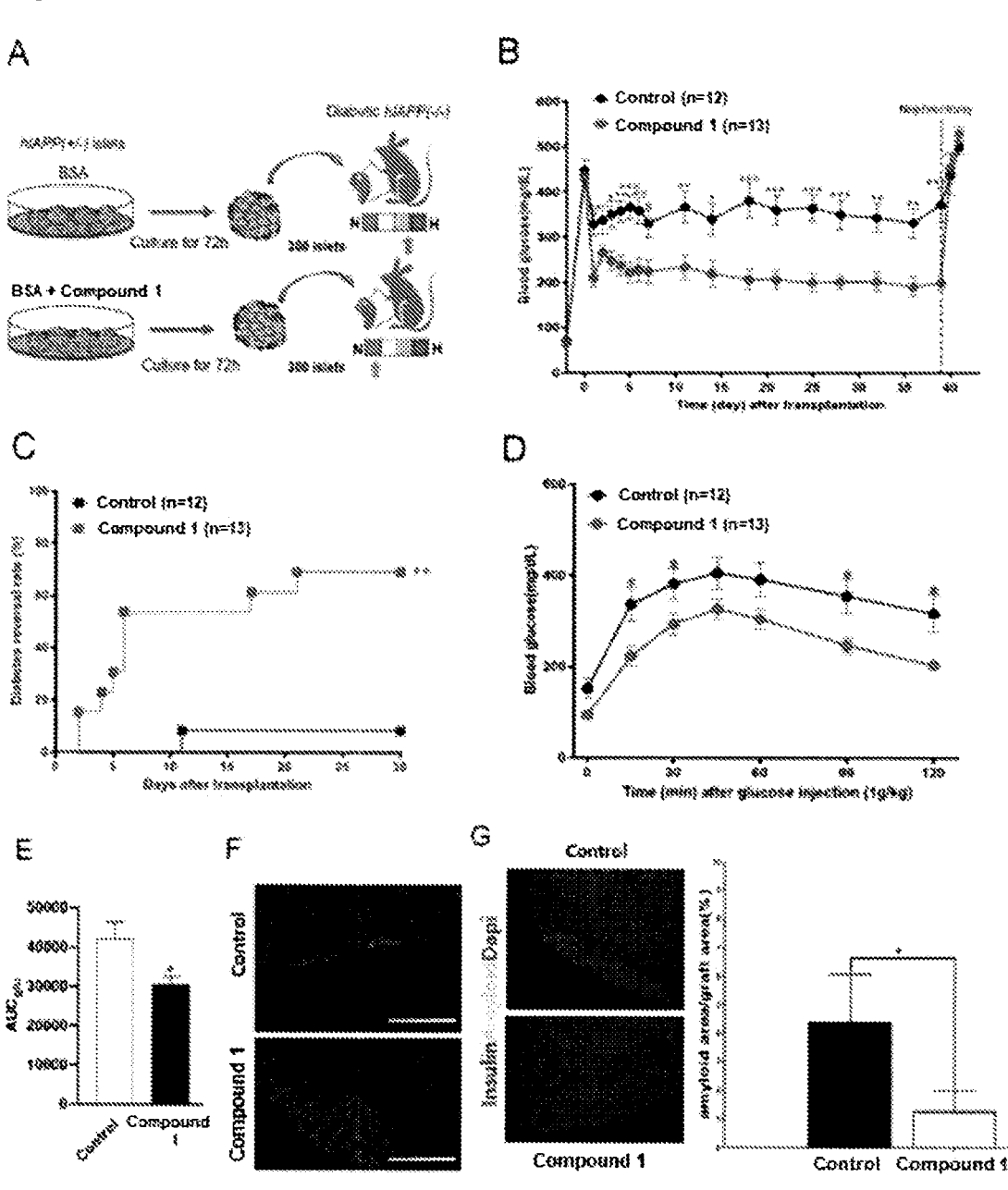

COMPOSITION FOR PROTECTING ISLET TRANSPLANTATION

CROSS-REFERENCE TO RELATED APPLICATION(S)

This application is a 35 U.S.C. 371 National Phase Entry Application from PCT/KR2021/004022 filed on Mar. 31, 2021, which claims the benefit of Korean Patent Application No. 10-2020-0039408 filed on Mar. 31, 2020 with the Korean Intellectual Property Office, the disclosures of which are incorporated herein by reference in their entirety.

TECHNICAL FIELD

The present invention relates to a composition having protective effect during islet transplantation. More specifically, the present invention relates to a composition for protecting islet transplantation comprising a compound of the following Formula 1 or a pharmaceutically acceptable salt thereof which can provide protective effect against oxidative stress and inflammation during islet transplantation:

[Formula 1]

wherein n, X, $R^1$, $R^2$, $R^3$, $R^4$, $R^5$ and $R^6$ are the same as defined herein.

BACKGROUND ART

Type 1 diabetes, or long-term type 2 diabetes, which is rapidly increasing in recent years, is highly dependent on insulin due to destruction of pancreatic $\beta$-cells, and the incidence of life-threatening hypoglycemia and diabetes complications is high. Islet transplantation refers to an operation in which a pancreas donated from a brain dead is biochemically treated to isolate pure islets, and then administered to a recipient. The purpose of surgery is to allow diabetic patients to control their blood sugar normally without insulin administration. Transplanted islets secrete insulin, allowing recipients to lead a normal life without insulin administration.

Allogeneic pancreatic islet transplantation has been a promising strategy for eliminating severe hypoglycemia and achieving normoglycemia in people with type 1 diabetes complicated by impaired awareness of hypoglycemia. However, substantial loss of transplanted islet mass during the peri-transplant period remains an important hurdle for the widespread clinical use.

During the peri-transplant period, hypoxia/reoxygenation-induced injury and release of damage-associated molecular patterns (DAMPs) such as high-mobility group box 1 (HMGB1) has been increasingly accepted as a potent activator of innate immunity and proinflammatory cytokine production. In contrast to apoptosis which is non-inflammatory or even anti-inflammatory mode of cell death, necroptosis or necrosis is highly immunogenic. At least in part, both DAMPs released from the necrotic cells and cell-intrinsic activation of nucleotide-binding oligomerization domain (NOD)-like receptor protein 3 (NLRP3) inflammasome during the necroptosis process are responsible for such immunogenicity.

Generation of mitochondrial reactive oxygen species (ROS), which induces opening of mitochondrial permeability transition pore (mPTP), is one of the key players promoting necroptosis and necrosis processes. The role of mitochondrial ROS in necroptosis and necrosis in transplanted islets could be critical because $\beta$-cells are known to be highly susceptible to oxidative stress due to low expression of the antioxidant enzyme genes such as catalase, superoxide dismutase and glutathione peroxidase. Therefore, oxidative stress generated during the various process of islet transplantation and hypoxia/reoxygenation-induced injury could play an essential role in significant $\beta$-cell damage and primary loss of transplant islets. In this context, various antioxidants have been used in few studies to provide possible effects on protection of islets against oxidative damage, leading to enhance islet viability and insulin secretion in vitro, and improve islet transplantation procedures. However, clinical translation of these approaches would require more potent efficacy and availability of clinical-grade materials. In addition, production of mitochondrial ROS has not been a specific target in previous studies and these studies primarily focused on the reduction of apoptosis.

DISCLOSURE OF INVENTION

Technical Problem

Accordingly, the technical problem of the present invention is the provision of a composition which can effectively protect islets at the time of islet transplantation.

Solution to Problem

In order to achieve the above object, the present invention provides a composition for protecting islet transplantation comprising as an active ingredient a compound of the following Formula 1 or a pharmaceutically acceptable salt thereof:

[Formula 1]

wherein
n is 0 or 1;
X is C or N, provided that n is 0 when X is N, and n is 1 when X is C;
$R^1$ is hydrogen or $C_1$-$C_6$ alkyl;
$R^2$ is phenyl or pyridine;
$R^3$ is hydrogen, halogen or $C_1$-$C_6$ alkyl;
$R^4$ is hydrogen, halogen, 2-carboxy-pyrrolidin-1-yl, pyrrolidin-1-yl, 4-acetic acid-1,3-thiazolin-2-yl, —$CH_2$-(1,1-dioxo-thiomorpholin-4-yl) or —$CH_2$-(2-oxopiperazin-4-yl);

R⁵ is hydrogen, $C_1$-$C_6$ alkyl or $C_3$-$C_6$ cycloalkyl; and

R⁶ is-D-W—R⁷, wherein D is cyclopentyl, cyclohexyl, pyrrolidine, tetrahydropyran, tetrahydrofuran or piperidine; W is a direct bond, —$SO_2$—, —CO— or —C(O) O—; and R⁷ is hydrogen, hydroxy or $C_1$-$C_6$ alkyl.

In one embodiment according to the present invention, the compound of Formula 1 may be (tetrahydropyran-4-yl)-[2-phenyl-5-(1,1-dioxo-thiomorpholin-4-yl)methyl-1H-indol-7-yl]amine of the following Formula 2:

In another embodiment according to the present invention, the pharmaceutically acceptable salt may include an acid-addition salt which is formed from an inorganic acid such as hydrochloric acid, sulfuric acid, nitric acid, phosphoric acid, hydrobromic acid and hydroiodic acid; an organic acid such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acid such as methanesulfonic acid, ethanesulfonic acid, benzenesulfonic acid and p-toluenesulfonic acid, which form non-toxic acid-addition salt including pharmaceutically acceptable anion. In addition, the pharmaceutically acceptable salt may include a pharmaceutically acceptable base-addition salt—for example, the salt with alkali metal or alkali earth metal such as lithium, sodium, potassium, calcium and magnesium; salts with amino acid such as lysine, arginine and guanidine; and an organic salt such as dicyclohexylamine, N-methyl-D-glucamine, tris(hydroxymethyl)methylamine, diethanolamine, choline and triethylamine, but is not limited thereto. The compound of Formula 1 according to the present invention may be converted into their salts by conventional methods, and the preparation of the salt could be easily carried out by a person skilled in the art based on the structure of Formula 1 without a separate explanation.

Islet (pancreatic islet) transplantation is an operation in which only insulin-producing islet cells from the pancreas are isolated and transplanted into a recipient, and is a representative example of cell therapy and not solid organ.

However, β-cells are vulnerable to oxidative stress due to their weak anti-oxidative defense systems. During islet isolation, various factors including hypothermia, mechanical stress, and exposure to collagenase contribute to generate oxidative stress and ultimately trigger cell death. Under low availability of oxygen and nutrients during the process of islet transplantation and revascularization, apoptosis, autophagy, necrosis and necroptosis occur in islets. Although apoptosis, in contrast to necrosis, usually does not involve inflammatory reactions, primary apoptosis in islets by hypoxia may induce immune activation presenting non-cleaved caspase-9 and caspase-3, not their cleaved forms. This indicates main cellular death process towards necrosis, which induces damage-associated molecular patterns (DAMPs) release, rather than secondary apoptosis. DAMPs are molecules such as HMGB1, dsDNA and uric acid released from the intracellular space and recognized mainly by Toll-like receptors (TLRs) involving innate immune system. As DAMPs are released during ischemia and reperfusion injury as the consequences of cellular death by necrosis and necroptosis and contribute to inflammation cascade in islet-graft failure, suppressing necrosis and necroptosis rather than apoptosis or autophagy may be a preferable strategy for reducing DAMPs release and associated immune responses during the period of islet transplantation.

HMGB1 is secreted by damaged or necrotic cells during cell death and acts as a DAMP signal and proinflammatory cytokine and relates to the pathogenesis of various inflammatory diseases. Several inflammatory cytokines such as IL-1β, IFN-γ and TNF-γ were also known to be responsible for inducing β-cell dysfunction and apoptosis through a series of intracellular signaling pathways, including ROS formation and JNK activation, and translocation of NF-κB. NF-κB is a transcription factor which controls NADPH oxidase, leading to generation of oxidative stress. The concerted action of proinflammatory cytokines induced the expression of inducible nitric oxide synthase (iNOS) and blockade of iNOS activity or increased expression of manganese superoxide dismutase (MnSOD) attenuated cytokine-induced NF-κB activation under in vitro conditions in insulin-producing cell lines.

To avoid the use of animal products for safety regulations, isolated human islets are commonly cultured in serum-deprived culture condition before clinical allogeneic intraportal islet transplantation. During the culture of islets under serum deprivation condition, islets are further exposed to diverse stresses in the culture medium, deprivation of nutrients, various proinflammatory cytokines, enzymes from the exocrine pancreas and deprivation of adequate oxygenation, and these stresses are harmful to β-cell, inducing accumulation of ROS in excess. In addition, it had been thought that toxicity of islet amyloid polypeptide (IAPP) is a cause of gradual decrease in the amount of β-cells and islet fibrosis in type 2 diabetes, and serum-deprived culture in euglycemic condition provokes toxic hIAPP oligomers accumulation. The inhibition of IL-1/IL-1 receptor axis can attenuate the inflammatory responses and functional impairment of islets caused by serum-deprived culture, but IL-1 blockade cannot attenuate accumulation of toxic oligomers during the serum-deprived culture.

The compound of Formula 1 according to the present invention can protect islets by reducing the amount of oxidative stress and reactive oxygen species (ROS) when treated while isolating islets.

In addition, when the compound of Formula 1 according to the present invention is treated during serum-deprived culture of isolated islets, the expression of c-jun N-terminal kinase, HMGB1 (high mobility group box-1) and proinflammatory cytokines (e.g., interleukin-113, interleukin-6 and tumor necrosis factor (TNF)-α) is decreased, and the accumulation of amyloid and toxic IAPP (islet amyloid polypeptide) oligomers is decreased due to potent mitochondrial reactive oxygen species (ROS) scavenging activity.

The compound of Formula 1 according to the present invention effectively protects islets when it is treated during islet isolation or serum-deprived culture of isolated islets through the mechanism of action as described above, thereby dramatically improving the diabetes reversal rate after islet transplantation.

In another embodiment according to the present invention, the composition of the present invention may further comprise a pharmaceutically acceptable carrier, if necessary. As used herein, the term "carrier" refers to a material that facilitates the administration of compounds into cells or tissues, and there is no particular limitation thereto.

Advantageous Effects of Invention

The composition of the present invention can significantly improve the success rate in islet transplantation by providing an excellent protective effect on islet cells.

BRIEF DESCRIPTION OF DRAWINGS

FIG. 1 shows the results of evaluating effects of Compound 1 during isolation on in vitro viability, function and pro-inflammatory cytokines expression of isolated $hIAPP^{+/-}$ mouse islets.

FIG. 2 shows the results of evaluating effects of Compound 1 during isolation on in vitro viability, function and pro-inflammatory cytokines expression of isolated C57BL/6 mouse islets.

FIG. 3 shows the results of evaluating effects of Compound 1 during isolation on post-transplantation in vivo outcomes of $hIAPP^{+/-}$ mouse islets.

FIG. 4 shows the results of evaluating effects of Compound 1 during serum-deprived culture on the cell viability and ROS in RINm5F cells and $hIAPP^{+/-}$ mouse islets.

FIG. 5 shows the results of evaluating effects of Compound 1 during serum-deprived culture on the cell viability and ROS in nonhuman primate (NHP) islets.

FIG. 6 shows the results of evaluating effects of Compound 1 during serum-deprived culture on in vitro viability, function, pro-inflammatory cytokines expression and oligomer accumulation of isolated $hIAPP^{+/-}$ mouse islets.

FIG. 7 shows the results of evaluating effects of Compound 1 during serum-deprived culture on post-transplantation in vivo outcomes of $hIAPP^{+/-}$ mouse islets.

MODE FOR THE INVENTION

Hereinafter, the present invention will be described in more detail through preparation examples and examples. However, these examples are only illustrative, and the scope of the present invention is not limited thereto.

I. Experimental Materials and Methods

1. Compound (Tetrahydropyran-4-yl)-[2-phenyl-5-(1,1-dioxo-thiomorpholin-4-yflmethyl-1H-indol-7-yl]amine (hereinafter referred to as "Compound 1") was prepared according to the method described in Example 36 of International Publication No. WO 2009/025478 A1.

2. Experimental Animals and Cell Line

Islets were isolated from heterozygous human islet amyloid polypeptide transgenic ($hIAPP^{+/-}$)FVB/N mice (Jackson Laboratory, Bar Harbor, ME, USA), $C_{58}BL/6$ mice (Orientbio, Sungnam, Korea), and cynomolgus monkeys (*Macaca fascicularis*; Orientbio, Sungnam, Korea). For additional in vitro studies, rat insulinoma cells (RINm5F cells) were treated with or without Compound 1 during culture under tert-butyl hydroperoxide (tBHP) exposure or serum deprivation condition. RINm5F cells were suspended in DMEM medium (Gibco, Grand Island, NY, USA) containing 100 IU/mL penicillin and 100 µg/mL streptomycin, and cultured at 37° C. in a fully humidified 5% $CO_2$ atmosphere. All experimental protocols in this study were approved by the Institutional Animal Care and Use Committee (IACUC) of Samsung Biomedical Research Institute.

3. Islet Isolation

Mouse islets were isolated from 10- to 12-week-old $hIAPP^{+/-}$ and $C_{57}BL/6$ mice as described previously. Briefly, 0.8 mg/mL of collagenase P (Roche, Indianapolis, IN, USA) in Hank's buffered saline solution (HBSS, Sigma-Aldrich, St. Louis, MO, USA) with or without 20 µM Compound 1 were infused into the common bile duct for mouse pancreas digestion. Islets were purified from the digested pancreas using a Ficoll (Biochrom, Berlin, Germany) gradient and washed several times with 1 xHBSS. Isolated islets were cultured while free-floating in 10 mL of RPMI 1640 (Gibco, Grand Island, NY, USA). The medium was supplemented with 10% heat-inactivated FBS (fetal bovine serum) at 37° C. and 5% $CO_2$ incubation prior to the ex vivo and in vivo studies.

4. Nonhuman Primate Islet Isolation

The dissected nonhuman primate (NHP) pancreas was injected intraductally with a cold Liberase MTF C/T solution (4 mL/g pancreas; Roche). Digestion and isolation were performed using Ricordi's automated isolation technique as described previously. All isolated NHP islets were cultured in a CMRL medium supplemented with 10% heat-inactivated porcine serum at 37° C. and 5% $CO_2$ incubation prior to the in vitro and in vivo studies.

5. Serum-Deprived Ex Vivo Culture of Isolated Islets

Purified $hIAPP^{+/-}$ FVB/N and C57BL/6J mouse were suspended in RPMI 1640 (Gibco, Grand Island, NY, USA) containing 100 IU/mL penicillin and 100 µg/mL streptomycin, and cultured at 37° C. in a fully humidified 5% $CO_2$ atmosphere. Purified NHP islets were suspended in CMRL 1066 medium (Coming Life Sciences, Tewksbury, MA; catalog number 99-663-CV) containing 100 IU/mL penicillin and 100 µg/mL streptomycin, and cultured at 37° C. in a fully humidified 5% $CO_2$ atmosphere. During the ex vivo culture of murine islets, three experimental groups were designated for experiments using $hIAPP^{+/-}$ FVB/N and $C_{57}BL/6J$ mice islets: medium supplemented with 10% FBS (Tissue Culture Biologicals, Los Alamitos, CA, USA; catalog number 101; FBS group), medium supplemented with 0.625% bovine serum albumin (Qbiogene, Carlsbad, CA, USA; catalog number BSA003; BSA group), and medium supplemented with 0, 0.1, 1, 10 and 20 µM Compoun 1 plus 0.625% BSA (BSA+Compound 1 group). In experiments using NHP islets, the medium was supplemented with 10% FBS (FBS group) and 0-20 µM Compound 1 plus 0.625% human serum albumin (HSA; Greencross, Yongin, Korea) to determine the optimal concentration of Compound 1 for treatment during the serum-deprived culture. Also, the medium was supplemented with 10% FBS (FBS group), 20 µM Compound 1 plus 10% FBS (FBS+Compound 1 group), 0.625% human serum albumin (HSA; Greencross, Yongin, Korea; HSA group), or 20 µM Compound 1 plus 0.625% HSA (HSA+Compound 1 group).

6. Evaluation of Islet Viability by Alamar Blue Assay

The viability of islets was evaluated using Alamar blue staining according to the manufacturer's protocol (Invitrogen, Grand Island, NY, USA). Briefly, islets isolated from $hIAPP^{+/-}$ mice were cultured at a density of 100 islet equivalents (IE) per well in 24-well plates with RPMI 1640 containing 10% FBS and 0.625% BSA with or without Compound 1. After 1 and 3 days, 10× Alamar blue solution was added directly to each well, and the islets were incubated at 37° C. for 4 hours with protection from direct light. The fluorescence intensity of each well was measured at 570/585 nm (excitation/emission) using a GloMax-Multi Plus Detection System (Promega, Fitchburg, WI, USA), and the values were normalized to a blank.

7. Acridine Orange/Propidium Iodide (AO/PI) Assay

Islet viability after isolation and culture was assessed using double fluorescence in acridine orange (0.67 μmon) and propidium iodide (75 μmon) (AO/PI) staining to visualize the living and dead islet cells simultaneously. Fluorescent imaging was performed with a fluorescence microscope (Nikon ECLIPSE 80i, Tokyo, Japan) and live and dead areas were quantified using NIS-Element AR 3.0 (Nikon). The islet viability (%) was calculated as living islet cells/total islet cells×100.

8. ATP Assay

ATP content of islets was assayed by a luminometric method. The samples were mixed with 200 μL of a commercially available lyophilized ATP monitoring reagent containing firefly luciferase and luciferin (ATP Biolumines-cence Assay KIT CLS II, Roche Diagnostics) at first reconstituted in an imidazole buffer (100 mM, pH 7.75). The emitted light was measured in a luminometer (LKB 1250 luminometer). The adenine nucleotide content in samples was determined after correction of the control (no islet or cell) and calculated by reference to ATP standards treated in the same manner as the samples.

9. Fluorescence-Based Intracellular Free Radical Detection and Lipid Peroxidation The oxidative stress levels in hIAPP$^{+/-}$ mouse islets were determined right after islet isolation and after ex vivo culture of isolated islets. The oxidative stress of the islets was quantified using a fluorescence-based intracellular ROS detection method and by estimating the concentration of malondialdehyde (MDA), a by-product of lipid peroxidation. The formation of total ROS, superoxide ion and nitric oxide was determined using a reactive oxygen species detection kit (ENZ-51011, Enzo Life Sciences, Farmingdale, New York, USA). The ROS content was measured by levels of DHR123 fluorescence. The kit was applied according to the manufacturer's protocol.

10. Glucose-Stimulated Insulin Secretion (GSIS) Assay

After hand-picking and washing with PBS, islets were seeded on 12-mm diameter insert wells (Merck Millipore, Billerica, MA, USA) with 10 islets per well, and preincubated with 60 mg/dL glucose in Kreb's-Ringer buffer (KRB: 129 mM NaCl, 4.8 mM KCl, 2.5 mM CaCl$_2$, 1.2 mM KH2PO4, 5 mM NaHCO$_3$, 10 mM HEPES, and 0.2% BSA) for 90 mM at 37° C. After washing, islets were incubated with 300 mg/dL glucose-KRB for 1 hour, followed by additional incubation with 60 mg/dL glucose-KRB for 1 hour. Insulin release into the supernatant by the mouse islets was measured by ELISA (ALPCO, Salem, NH, USA) and a multiplex kit (Merck Millipore), respectively.

11. RNA Isolation and cDNA Synthesis

Harvested islets were treated with 500 μL Trizol (Life Technologies, Grand Island, NY, USA), and then 100 μL of chloroform was added. After incubation at 4° C. for 5 minutes, the mixture was centrifuged at 12,000 rpm for 15 minutes, and 250 μL of isopropyl alcohol was added to precipitate total RNA. RNA pellets were washed with 75% ethanol, and RNA was eluted from pellets using RNase-Free water (WelGene, Daegu, South Korea). RNA purity was assessed by NanoDrop (Thermo Scientific, Wilmington, DE, USA) and agarose gel electrophoresis. The purity of RNA ranged from 1.9 to 2.0 based on the ratio of optical densities (OD) of 260/230 and 260/280. Total RNA was reverse transcribed to quantify the expression of genes using the SuperScript™ II reverse transcription system (Life Technologies) according to the manufacturer's protocol.

12. Real-Time Quantitative Reverse Transcription (qRT)-PCR

Real-time qRT-PCR was performed using gene-specific primer pairs (Table 1). Amplified PCR products were normalized to the β-actin PCR product amplified from the same sample. PCR products were separated on 1% agarose gels, and images were obtained using a Gel Doc™ XR instrument (Bio-Rad, Hercules, CA, USA). To quantify the expression level of genes, real-time PCR was performed using a SYBR premix kit (Takara Bio Inc., Tokyo, Japan) and an ABI Prism 7000 (Applied Biosystems, Foster City, CA, USA) according to the manufacturers' protocols.

TABLE 1

| Genes | Gene-specific primer sequence | |
| | Forward | Reverse |
| --- | --- | --- |
| | Mouse | |
| β-actin | GGCTGTATTCCCCTCCA TCG | CCAGTTGGTAACAATGCCA TGT |
| IL-1β | TCAGGCAGGCAGTATCA CTC | GAAGGTCCACGGGAAAGAC AC |
| IL-6 | CTATACCACTTCACAAG TCG | GAATTGCCATTGCACAACT CT |
| TNF-α | CTGAACTTCGGGGTGAT CGG | GGCTTGTCACTCGAATTTT GA |
| C-jun | CCTGTCCCCTATCGACA TGG | CTTTTCCGGCACTTGGAGG |
| HMGB1 | CGAGAGGCAAAATGTCC TCA | TCATAACGAGCCTTGTCAG C |

IL-1β: Interleukin-1 beta;
IL-6: Interleukin-6;
TNF-α: Tumor necrosis factors-alpha;
HMGB1: High mobility group box 1

13. In Vivo Islet Function of hIAPP$^{+/-}$ Islets

A marginal mass renal subcapsular islet transplantation model was used to assess the in vivo islet function of hIAPP$^{+/-}$ mice. To induce diabetes, 180 mg/kg of streptozotocin (STZ, Sigma-Aldrich) was administered to 8- to 10-week-old FVB/N mice. Mice were considered to have diabetes when two consecutive blood glucose level readings were higher than 300 mg/dL. Equal amounts (400 IEQ of islets per recipient) of islets isolated from hIAPP$^{+/-}$ mice were allocated to the following two groups: culture medium supplemented with 0.625% BSA (BSA group) and 0.625% BSA plus Compound 1 (BSA+Compound 1 group) to evaluate the combined effect of Compound 1 on islet mass and function during ex vivo culture. After culture for 72 hours, islets were transplanted into the renal subscapular space of diabetic hIAPP$^{+/-}$ mice. The IE number was calculated using the Ricordi algorithm by classifying islets according to their diameter. After islet transplantation, non-fasting blood glucose levels were measured three times a week for the first 2 weeks and twice a week for the last 2 weeks.

14. Histological Analysis

At 4 weeks after transplantation, the transplantation site on the kidney of mouse were removed and embedded in paraffin. Immunohistochemical staining is briefly explained in the following. After deparaffinization, 4-μm tissue sections were stained with the polyclonal guinea pig anti-insulin antibody (1:1000, A0546, DAKO, Denmark), gluca-con (1:500, ab92517, abcam, United Kingdom) and amyloid (1:2500, #44-344, Invitrogen). Stained slides were observed using an Olympus BX40 light microscope (Olympus, Japan) with ×10/22 numeric aperture and ×40/0.75 numeric aperture objectives. Photographic images were collected with a digital camera (Olympus DP50) and analyzed using the Image-Pro Plus 5.1 software.

For quantification of the DAB-labeled β-cells, all slides were imaged at 10× on a Vectra 3.0 automated quantitative pathology imaging system and analyzed using inForm software (all from Perkin-Elmer, Waltham, MA, USA). The transplanted renal tissue sections were scanned for image acquisition and then to set the transplanted tissue segmentation, a number of representative regions of transplanted islet cells and regions to be excluded from the analysis such as renal tissues were examined by learn-by-example interface. For the β-cell segmentation, a spectral library was used to identify the hematoxylin-stained nuclei and the DAB-stained cytoplasm (β-cells) within the transplanted tissue. With these training sets, the algorithm for identifying only the DAB-stained cells in the transplanted tissue was verified. All the captured 10× images were analyzed, and the DAB-stained transplanted β-cells were counted.

15. Evaluation of hIAPP Oligomer Accumulation

Accumulation of hIAPP oligomers was evaluated using sections of hIAPP$^{+/-}$ mice islets stained with A11 Ab (anti-oligomer antibody, Invitrogen) and insulin antibody (Dako). Islets were blocked with 10% normal donkey serum and incubated with primary rabbit anti-oligomer (1:100). Islets were washed and incubated with secondary Cy3-conjugated anti-rabbit antibody for 1 hour. After washing, sections were stained with a guinea pig anti-insulin primary antibody (1:500; Dako) followed by an Alexa Fluor 488 anti-guinea pig secondary antibody (1:200; Jackson ImmunoResearch Laboratories). Sections were mounted after counterstaining with 40,6-diamidino-2-phenylindole (DAPI). To quantify accumulation of hIAPP oligomers per islet, the proportion of A11-stained cells among total DAPI+islet cells was determined using confocal microscopy.

16. Evaluation of Amyloid Accumulation

The sections of islet grafts under the kidney capsule were examined for islet amyloid after 0.5% thioflavin S staining (Sigma) and for β-cells using insulin immunostaining with a guinea pig anti-insulin antibody (1:500; Dako, Carpenteria, CA) followed by Cy3-conjugated anti-guinea pig secondary antibody (1:200; Jackson ImmunoResearch Laboratories, West Grove, PA). Sections were mounted after staining with DAPI. To quantify accumulation of amyloid per section, the percent proportion of thioflavin S-stained cells (green) among total islet graft site (green+red+blue portion) was determined using confocal microscopy. Original magnification is 100× for panels.

17. Statistical Analysis

Results are expressed as means±standard deviations (SD) or medians and interquartile ranges, as appropriate. Continuous variables were compared using Student's t-test, one-way analysis of variance (ANOVA), or the Mann—Whitney U test, as appropriate. Longitudinal data were analyzed by two-way ANOVA with Bonferroni post hoc testing using Graphpad Prism 5 (GraphPad Software, La Jolla, CA, USA). A p value<0.05 was accepted as statistically significant for comparisons.

II. Results

1. Protective Effects Against Oxidative Stress and Proinflammatory Responses During Islet Isolation To evaluate the effect of Compound 1 during the islet isolation, islets from hIAPP$^{+/-}$ FVB/N mice were isolated by collagenase with and without supplementation with 20 μM of Compound 1. The relative ex vivo cell viability assessed by Alamar blue assay was significantly increased in the Compound 1 treated group compared to those non-treated group (FIG. 1A). In addition, Compound 1 treatment during islet isolation presented significantly elevated levels of ATP compared to Compound 1 non-treated group (FIG. 1B). Also, ROS contents and oxidative stress levels in islets treated with Compound 1 during the islet isolation were markedly decreased compared to control islets without Compound 1 treatment (FIGS. 1C and 1D). The stimulation index obtained in the glucose-stimulated insulin secretion (GSIS) assay, presenting the in vitro islet function, showed comparable values between two groups (FIG. 1E). Next, we also examined the transcriptional expression of c-Jun N-terminal kinases and high mobility group box-1 (HMGB1), and proinflammatory cytokines including interleukin (IL)-1β, IL-6, and tumor necrosis factor (TNF)-α in the culture medium after isolation with and without supplementation of Compound 1. These transcriptional expression levels were significantly decreased in Compound 1 treated group compared to non-treated group (FIG. 1F). These results were reproduced in wild type C57BL/6 mouse islets (FIG. 2).

2. Effect on Improvement of Post-Tranplantation Outcomes

Figure 3:
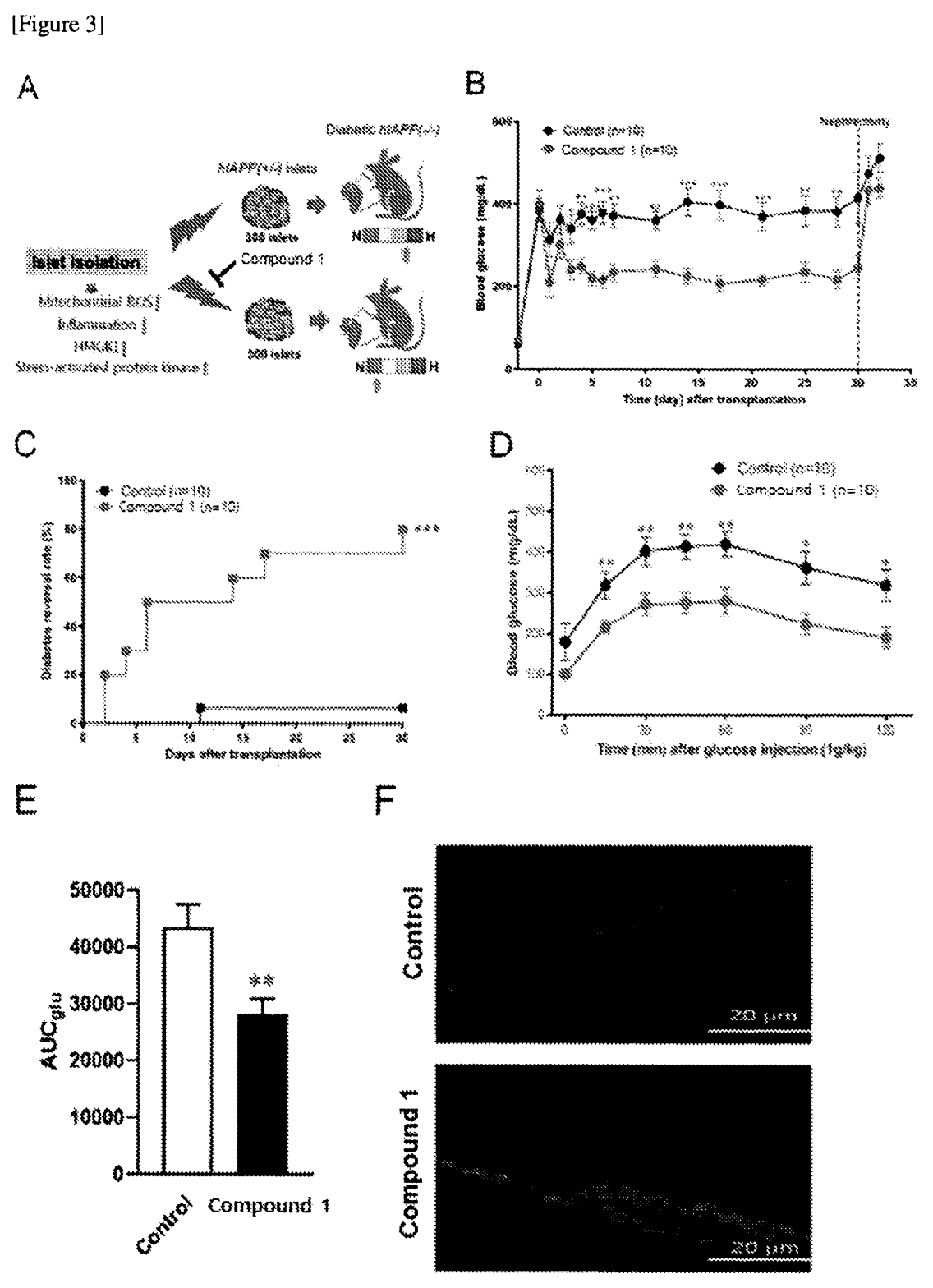

To examine the effect of supplementation of Compound 1 during islet isolation in vivo, marginal mass of islets, isolated with or without supplementation of Compound 1, were transplanted into renal subcapsular space of streptozotocin (STZ)-induced diabetic hIAPP$^{+/-}$ FVB/N mice (FIG. 3A). The post-transplant glucose levels of Compound 1 treated group were markedly lower than those of non-treated group and removal of the grafted kidney confirmed regain of hyperglycemia in the Compound 1 treated group (FIG. 3B). Compound 1 group demonstrated better post-transplantation outcomes, in terms of diabetes reversal rate and glucose levels during the intraperitoneal glucose tolerance test (IP-GTT), compared to those of control group (FIGS. 3C, 3D and 3E). Compound 1 group presented greater proportion of insulin positive area in the grafted tissue compared to that of control group (FIG. 3F).

3. Protection of hIAPP$^{+/-}$ Transgenic Mice and NHP Islets During Serum-Deprived Culture We examined the effect of supplementation of Compound 1 on tert-butyl hydroperoxide (tBHP) exposure or islet culture under serum-deprived condition. Although RINm5F cells exposed to tBHP exerted LDH release and ROS formation, cellular toxicity and ROS contents were markedly reduced after the supplementation of Compound 1 (FIGS. 4A and 4B). The relative cell viability of rat insulinoma cells (RINm5F cells) and islets from hIAPP$^{+/-}$ FVB/N mice significantly increased serum deprivation-induced cell toxicity by dose-dependent manner from 0.1 μM to 20 μM (FIGS. 4C and 4D). Supplementation of medium with Compound 1 during serum-deprived culture condition also decreased serum deprivation-induced ROS in RINm5F cells and islets from hIAPP$^{+/-}$ FVB/N mice by dose-dependent manner from 0.1 μM to 20 μM (FIGS. 4E and 4F). Similar results were observed in NHP islets (FIGS. 5A, 5B and 5C).

FIG. 6A shows cell viability of hIAPP$^{+/-}$ FVB/N mice islets during serum-deprived culture with or without Compound 1 supplementation assessed by AO/PI staining. Compared to the FBS-treated islets, islets cultured with BSA for 72 hours experienced greater cell death showing the positivity of red PI-positive cells and the impaired cell viability significantly improved by supplementation of Compound 1 (FIGS. 6A and 6B). Transcript levels of TNF-α, IL-1β, IL-6, c-JUN and HMGB1 after 1 and 3 days of ex vivo culture were significantly attenuated in the BSA+Compound 1 group than those in the BSA group (FIGS. 6C and 6D). For evaluating the function of islets, significantly increased stimulation index was observed in islets from hIAPP$^{+/-}$ mouse when Compound 1 was added to the medium during serum-deprived culture condition (FIG. 6E). After culture in medium with and without Compound 1 for 72 hours under serum deprived culture conditions, proportion of accumulation of hIAPP oligomers in hIAPP$^{+/-}$ islets was significantly decreased in BSA+Compound 1 group compared to BSA group (FIG. 6F).

4. Improvements of Post-Transplantation Glycemic Outcomes and Graft Islet Amyloid Accumulation We investigated whether supplementation of medium with Compound 1 during serum-deprived culture improves posttransplantation outcomes in in vivo mouse models. A marginal mass of islets from hIAPP$^{+/-}$ FVB/N mice were cultured with and without supplementation of Compound 1 for 72 hours and transplanted into subrenal subcapsular of STZ-induced diabetic hIAPP$^{+/-}$ FVB/N mice (FIG. 7A). The Compound 1 group demonstrated significantly better posttransplantation outcomes including posttransplant glucose levels, diabetes reversal rate, and glucose levels and AUC of glucose during IPGTT (FIGS. 7B, 7C, 7D and 7E). The insulin positive area in the grafted tissue was greater in Compound 1 group than the proportion in the control group (FIG. 7F). In addition, proportion of accumulation of amyloid was significantly reduced in the sections of islet grafts from Compound 1 group compared to the control group (FIG. 7G).

III. Discussion

Supplementation of Compound 1 during islet isolation resulted in increased in vitro islet cellular viability, and attenuated oxidative stress, reactive oxygen species (ROS) contents, and the expression of c-Jun, HMGB1 and proinflammatory cytokines. In addition, in vivo studies confirmed improved post-transplantation outcomes by treatment of Compound 1 during islet isolation.

Furthermore, Compound 1 protected against serum deprivation-induced impairment of in vitro islet viability. More importantly, supplementation of medium with Compound 1 during serum-deprived culture significantly reduced accumulation of amyloid as well as toxic IAPP oligomers, and improved in vivo islet graft function.

From these results, advantageous effects can be confirmed according to supplementation of Compound 1 during islet isolation as well as serum-deprivation culture in the process of islet transplantation.

The invention claimed is:

1. A method of protecting islets, comprising treating a pancreas during isolation of islets, or treating isolated islets during serum-deprived culture of isolated islets, with a compound of the following Formula 1 or a pharmaceutically acceptable salt thereof:

[Formula 1]

wherein n is 0 or 1;

X is C and n is 1;

$R^1$ is hydrogen or $C_1$-$C_6$ alkyl;

$R^2$ is phenyl;

$R^3$ is hydrogen or $C_1$-$C_6$ alkyl;

$R^4$ is $CH_2$-(1,1-dioxo-thiomorpholin-4-yl) or $CH_2$-(2-oxopiperazin-4-yl);

$R^5$ is hydrogen, $C_1$-$C_6$ alkyl or $C_3$-$C_6$ cycloalkyl; and $R^6$ is tetrahydropyran or tetrahydrofuran, wherein the compound of Formula 1 protects islets by reducing amounts of oxidative stress and reactive oxygen species (ROS).

2. The method according to claim 1, wherein the compound of Formula 1 is (tetrahydropyran-4-yl)-[2-phenyl-5-(1,1-dioxo-thiomorpholin-4-yl)methyl-1H-indol-7-yl]amine of the following Formula 2:

3. The method according to claim 1 wherein the compound of Formula 1 reduces the expression of c-jun N-terminal kinase, high mobility group box-1 (HMGB1), and and proinflammatory cytokines.

4. The method according to claim 3, wherein the proinflammatory cytokines are interleukin-1β (IL-1β), interleukin-6 (IL-6), and tumor necrosis factor-α (TNF-α).

5. The method according to claim 1, wherein the compound of Formula 1 reduces the accumulation of amyloid and toxic islet amyloid polypeptide (IAPP) oligomers.

* * * * *